United States Patent
Nuss et al.

(10) Patent No.: US 11,358,505 B2
(45) Date of Patent: Jun. 14, 2022

(54) SEAT ARMREST

(71) Applicants: Ralph Nuss, Poppenricht (DE); Hubert Keller, Weiherhammer (DE)

(72) Inventors: Ralph Nuss, Poppenricht (DE); Hubert Keller, Weiherhammer (DE)

(73) Assignee: GRAMMER AG, Ursensollen (DE)

( * ) Notice: Subject to any disclaimer, the term of this patent is extended or adjusted under 35 U.S.C. 154(b) by 0 days.

(21) Appl. No.: 16/924,629

(22) Filed: Jul. 9, 2020

(65) Prior Publication Data

US 2021/0009019 A1     Jan. 14, 2021

(30) Foreign Application Priority Data

Jul. 10, 2019   (DE) .......................... 102019004759.1

(51) Int. Cl.
  *B60N 2/75*    (2018.01)
  *A41D 13/11*   (2006.01)
  *A61F 9/04*    (2006.01)

(52) U.S. Cl.
  CPC .......... *B60N 2/793* (2018.02); *A41D 13/1184* (2013.01); *A61F 9/045* (2013.01); *B60N 2/767* (2018.02); *B60N 2/797* (2018.02); *A61H 2201/1604* (2013.01)

(58) Field of Classification Search
  CPC ......... B60N 2/793; B60N 2/797; B60N 2/767
  See application file for complete search history.

(56) References Cited

U.S. PATENT DOCUMENTS

| 3,926,473 | A | * | 12/1975 | Hogan | .................. | B60N 2/793 297/115 |
| 5,752,740 | A | * | 5/1998 | Volkmann | ................ | B60R 7/04 297/188.19 |
| 6,045,173 | A | * | 4/2000 | Tiesler | .................. | B60N 3/102 296/37.8 |
| 6,616,205 | B2 | | 9/2003 | Bruhnke | | |
| 9,409,502 | B2 | | 8/2016 | Anderson | | |
| 9,713,972 | B2 | | 7/2017 | Bozio et al. | | |
| 10,023,088 | B2 | * | 7/2018 | Anderson | .............. | B60N 2/793 |
| 10,358,069 | B2 | * | 7/2019 | Anderson | .............. | B60N 2/767 |

(Continued)

FOREIGN PATENT DOCUMENTS

| DE | 19643051 A | 11/1997 |
| DE | 10032657 A | 8/2002 |
| DE | 10110330 A | 10/2002 |

(Continued)

*Primary Examiner* — Philip F Gabler
(74) *Attorney, Agent, or Firm* — Andrew Wilford

(57) ABSTRACT

The invention relates to an armrest (10) for a seat, in particular for a vehicle seat, having a base (11) to which at least one container (18) having a cavity (27) is allocated, having an arm support (12) that is pivotable relative to the container (18) between a lower end position and an upper end position, having an arm support face (13), wherein at least one housing wall (19*a*, 19*b*, 19*c*) is allocated to the arm support (12), said housing wall (19*a*, 19*b*, 19*c*) being connected to the arm support (12) so as to move therewith in such a way that it closes an intermediate space arising between a stop face (25) of the arm support (12) and a support face (26) on the base part (11) when the arm support (12) pivots up, wherein the arm support (12) comprises an opening (16) through which access to the interior space (27) is possible.

13 Claims, 4 Drawing Sheets

(56) References Cited

U.S. PATENT DOCUMENTS

2021/0009019 A1* 1/2021 Nuss .................. B60N 2/767
2021/0170952 A1* 6/2021 Nuss .................. B60R 7/04

FOREIGN PATENT DOCUMENTS

| DE | 102007024000 A1 | 11/2008 |
|----|-----------------|---------|
| DE | 102008005642 A | 7/2009 |
| FR | 2877614 A1 | 11/2004 |

* cited by examiner

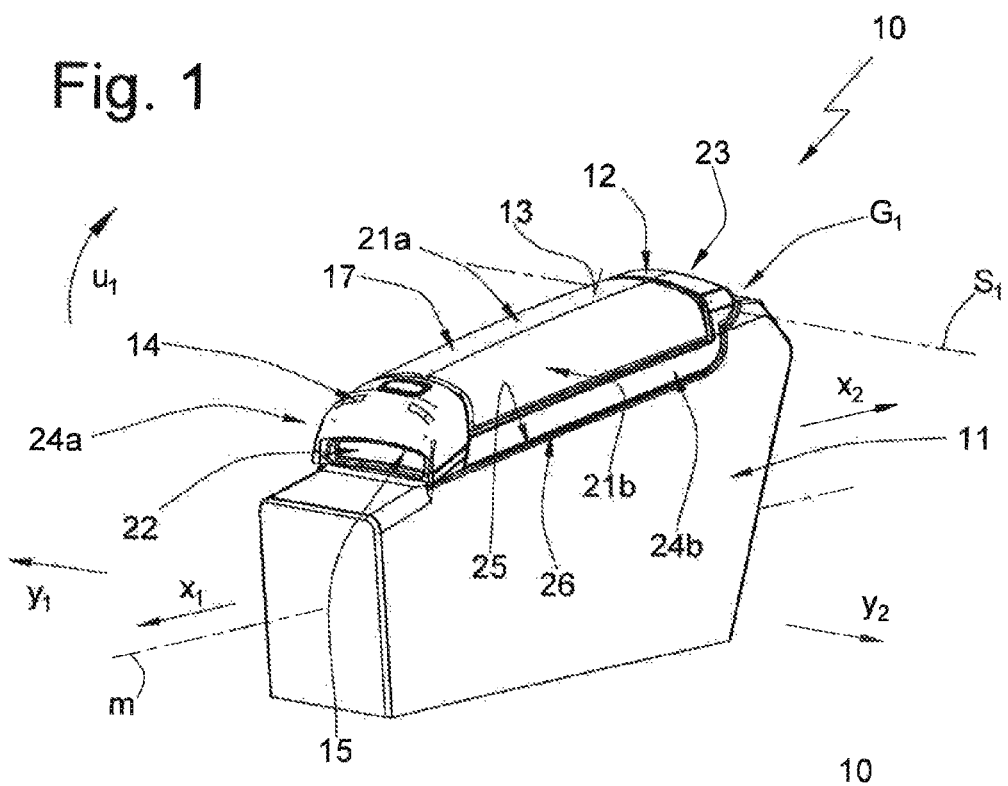
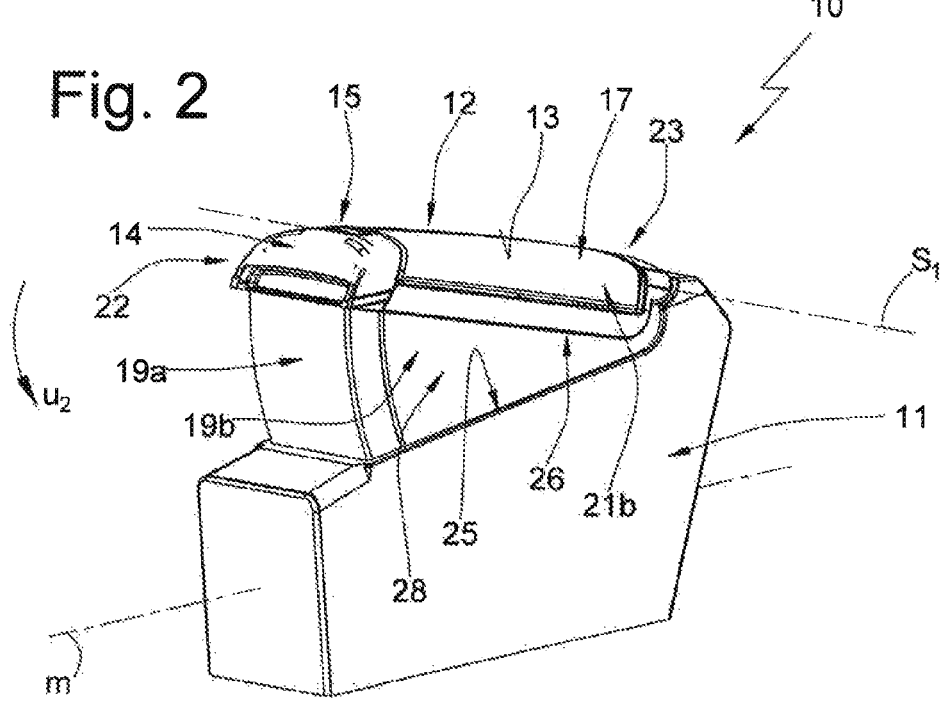

SEAT ARMREST

FIELD OF THE INVENTION

The invention relates to an armrest for a seat, in particular the seat of a vehicle. A vehicle within the meaning of the invention can be an air, land or water vehicle.

BACKGROUND OF THE INVENTION

An armrest is known from DE 101 10 330. The armrest is part of a center console and comprises an arm support part that can be adjusted forward and backward and comprises an opening that is closed using a lid that is movable between an open position and a closed position. The arm support is held on a height-adjustably mounted frame, in which a storage compartment is formed.

In DE 100 32 657, a center console with an armrest is described. Under the armrest, a first stowage compartment and a second stowage compartment are formed. An arm support is pivotable about a pivot axis and can be opened in such a way as to allow access to the first or second stowage compartment. In an embodiment illustrated in FIG. 4, the arm support is allocated to an external housing 30 that is vertically adjustable in relation to an internal housing 28. The adjustment takes place using guides and can form a straight or a curved path.

From DE 196 43 051, a coverable container for seat-side allocation in vehicles is disclosed. The container comprises a housing 10 with a housing opening 101 that can be closed by an arm support 11. The arm support 11 is pivotably mounted and can be locked in various pivot positions.

From DE 10 2008 005 642, an armrest is known that is formed in a center console of a motor vehicle. The armrest comprises a receptacle that is in a pivotable housing. The receptacle can be closed by a pivotable lid. In addition, a control panel is allocated to the housing that is likewise pivotable with the housing.

OBJECT OF THE INVENTION

It is the object of the present invention to create an armrest having a simple construction, wherein an arm support can be set in various positions.

SUMMARY OF THE INVENTION

The armrest comprises a base part that is in a fixed manner relative to the vehicle. The base part can be formed e.g. by a center console. Alternatively, the base part can be formed e.g. by a frame or a housing that is secured to the vehicle. A container on the base part forms a cavity in which objects can be accommodated. The container comprises an opening via which the cavity is accessible.

On the base part, an arm support is pivotal relative to the container. The arm support forms a pivot joint with the base part, for example. The arm support is pivotable between a lower end position and an upper end position. In the lower end position, a lower face of the arm support lies in contact with an upper support face of the base part. When the arm support has been moved from the lower end position toward the upper end position, its lower face is spaced from the upper support face of the base. In the upper end position, for example a stop face of the arm support and a stop face of the base part or of another part secured to the vehicle cooperate.

The armrest comprises a locking device with which the arm support can be releasably locked in various pivot positions in steps or continuously. The locking device can be adjusted between a locked position and a released position by actuation. The locking device comprises first locking means allocated to the base and second locking means allocated to the arm support that can be releasably engaged.

Housing walls are allocated to the arm support that close an intermediate space between the arm support and the container when the arm support is pivoted up. In other words, when the arm support is moved from a lower end position to a position in which the arm support has been pivoted by a particular pivot angle toward the upper end position, the intermediate space between the arm support and the container is closed by the housing walls such that an additional space is created that forms a passage that connects an opening of the arm support to the cavity of the container.

The intermediate space can be formed e.g. between a lower face of the arm support and an upper support face of the base. In the lower end position, the lower face and the upper support face are then in contact. In this way, the cavity of the container can only be reached via the opening.

According to one embodiment, the opening of the arm support can be closed by a lid that is movable between an open position and a closed position. The lid is mounted pivotably on the arm support, for example. The lid can have one or more parts. The lid can be movable in any position of the arm support between the open position and the closed position.

The opening is e.g. in a region of the arm support face of the arm support.

An outer face of the lid forms e.g. at least part of the arm support face. For example, the entire arm support face can be formed by the outer face of the lid. Alternatively, for example, only part of the outer face of the arm support can be formed by the outer face of the lid.

At least one slot is formed in the base, for example, in which slot the housing walls can be at least partially stowed. In this way, the housing walls are not visible in the lowest position of the arm support but only move out of the slot when the arm support pivots up.

The housing wall delimits the cavity with regard to at least three spatial directions, for example. The housing wall can be formed by separate parts or by one part.

The housing wall forms a passage, for example, in such a way that the cavity of the container is accessible only via the opening of the arm support. The passage connects the opening of the arm support and the opening of the container to each other, for example.

The lid can be formed e.g. in one piece or has e.g. at least two lid parts that can be moved together or separately.

The arm support is pivotable e.g. between the lower end position and the upper end position over a pivot angle of about 20° to 45°.

On a front end region, facing away from the pivot axis, the arm support has e.g. a control panel for switching and controlling equipment internal and/or external to the vehicle.

An embodiment of the invention is described by way of example in the following description of the figures, with reference to the schematic drawings. For the sake of clarity—including where different embodiments are concerned—identical or comparable parts or elements or regions are labeled with identical reference signs, with the addition of lower-case letters in some cases.

All features disclosed are, in their own right, essential to the invention. The disclosure content of the cited documents and of the described devices of the state of the art is hereby incorporated in full into the disclosure of the application, including for the purpose of taking up individual or multiple features of the subject matters disclosed there in one or more claims of the present application. Such modified embodiments—even if they are not illustrated in the drawings—are also comprised by the invention.

BRIEF DESCRIPTION OF THE DRAWING

The figures show the following:

FIG. 1: a perspective diagram of the armrest where the arm support is in a lower position and the lid is in a closed position, FIG. 2: the armrest according to FIG. 1 where the arm support is in an upper position.

SPECIFIC DESCRIPTION OF THE INVENTION

Figure 3:
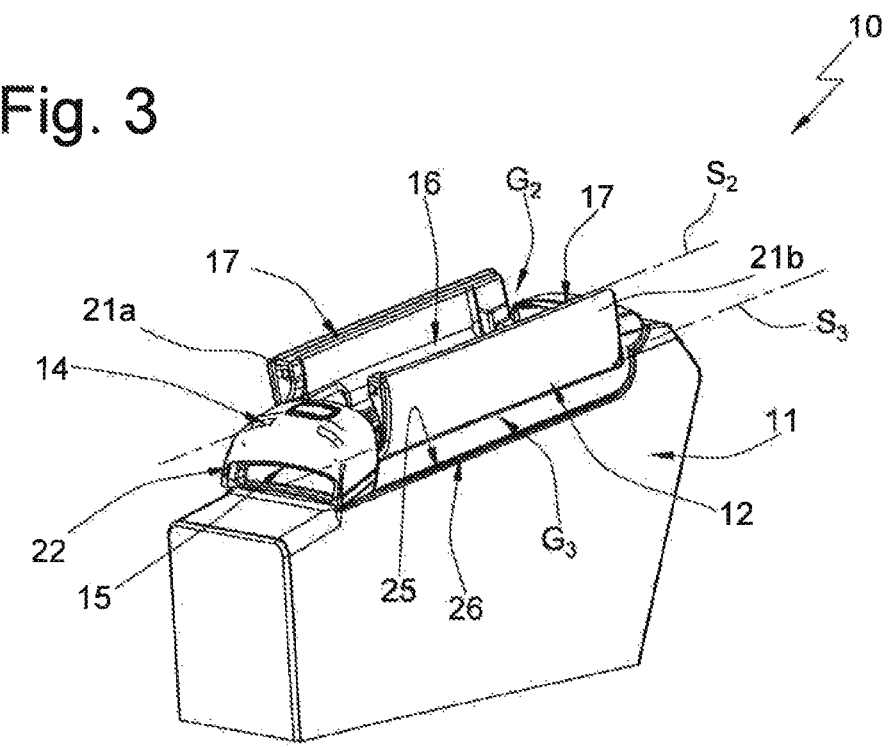
FIG. 3: the armrest according to FIG. 1 where a lid is in an open position.
Figure 4:
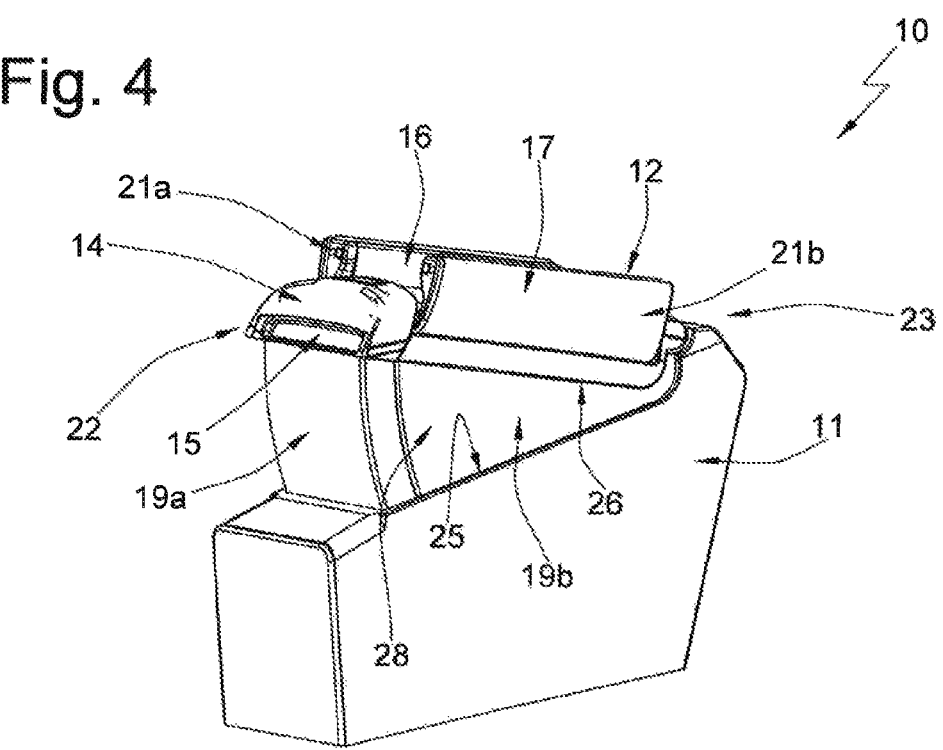
FIG. 4: the armrest according to FIG. 2 where the lid is in the open position.

An armrest as a whole is labelled in the figures with the reference numeral 10.

The armrest 10 is in a vehicle e.g. in such a way that a longitudinal central axis m of the armrest 10 extends parallel to directions $x_1$ and $x_2$ that respectively correspond to forward and reverse directions of travel. The armrest 10 can be e.g. between two seats in a front row of seats or between two seats in a back row of seats of the vehicle. Alternatively, however, other arrangements and orientations of the armrest 10 are also possible.

The armrest 10 comprises a base 11 that in the present example is part of a center console. An arm support 12 is held on the base 11 pivotably about a pivot axis $S_1$ and forms a pivot joint $G_1$ with the base 11. In FIG. 1 the arm support 12 is shown in the lower end position. FIG. 2 shows the armrest 10 with the arm support 12 in the upper end position. From the lower end position according to FIG. 1 the arm support 12 is pivotable in a direction $u_1$ into the upper end position. From the upper end position according to FIG. 2 the arm support 12 is pivotable in a direction $u_2$ into the lower end position.

A back end region 23 of the arm support is located close to the pivot joint G1, while a front end region 22 is located on a side of the arm support 12 facing away from the joint G1 with respect to the central axis m.

The arm support 12 comprises an arm support face 13, on which a vehicle occupant can rest his arm. A control panel 14 is in a front region of the arm support face 13. On the control panel 14, various operating elements can be controlled with which different vehicle functions or separate equipment, such as telephone, music equipment that is internal or external to the vehicle etc., can be switched or controlled.

Furthermore, the control panel 14 comprises an actuation of a locking device 15 of the armrest 10. Its actuation takes place here at a front end of the control panel 14. In the upper and lower end positions as well as in intermediate positions, the arm support 12 can be releasably locked by the locking device 15. The locking device 15 comprises first locking elements (not shown here) allocated to the base 11 and second locking elements (not shown here) allocated to the arm support 12. The design of the locking is known to a person skilled in the art. No further details of the locking will be given here.

According to FIG. 3, the arm support 12 comprises an opening 16 that can be closed by a lid 17. In any pivot position of the arm support 12, the lid 17 can be moved between a closed position (see e.g. FIG. 1) and an open position (see e.g. FIG. 3). The type of lid 17 is unimportant for the invention. Lids other than the lid 17 described here can also be used.

In the present embodiment the lid 17 is a so-called butterfly lid that comprises two lid parts 21a and 21b. The lid part 21a is pivotable about a pivot axis $S_2$ (see FIG. 3) that extends parallel to the central axis m and is in a side region 24a of the arm support 12. The lid part 21a forms a pivot joint $G_2$ with the base 11. The lid part 21b is pivotable about a pivot axis $S_3$ that likewise extends parallel to the central axis m and is in a side region 24b of the arm support 12. The lid part 21b forms a pivot joint $G_3$ with the base 11.

Figure 5:
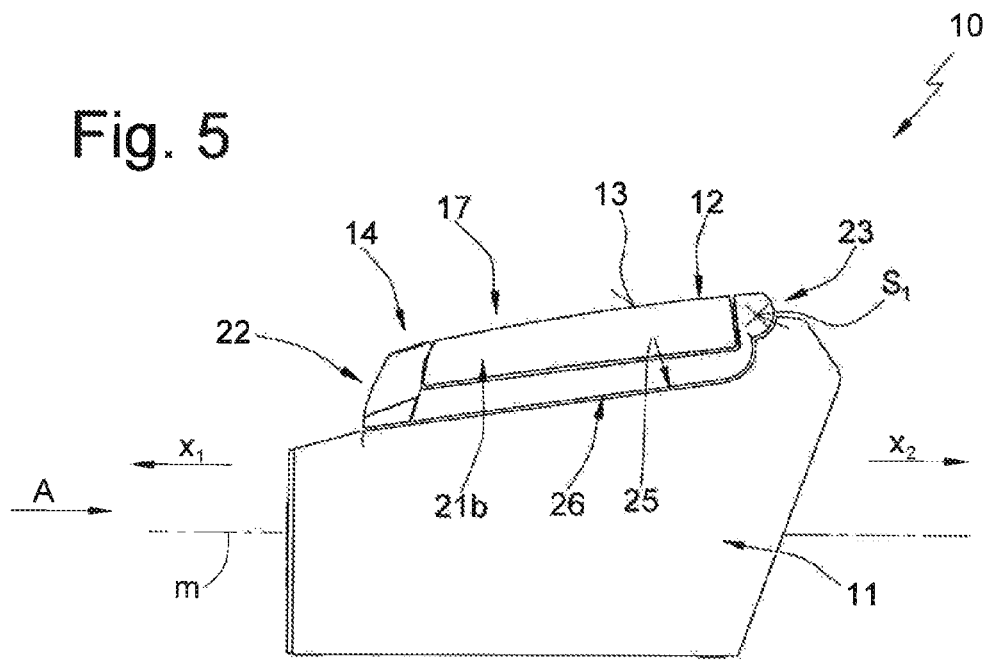
FIG. 5: a side view of the armrest as in FIG. 1.
Figure 6:
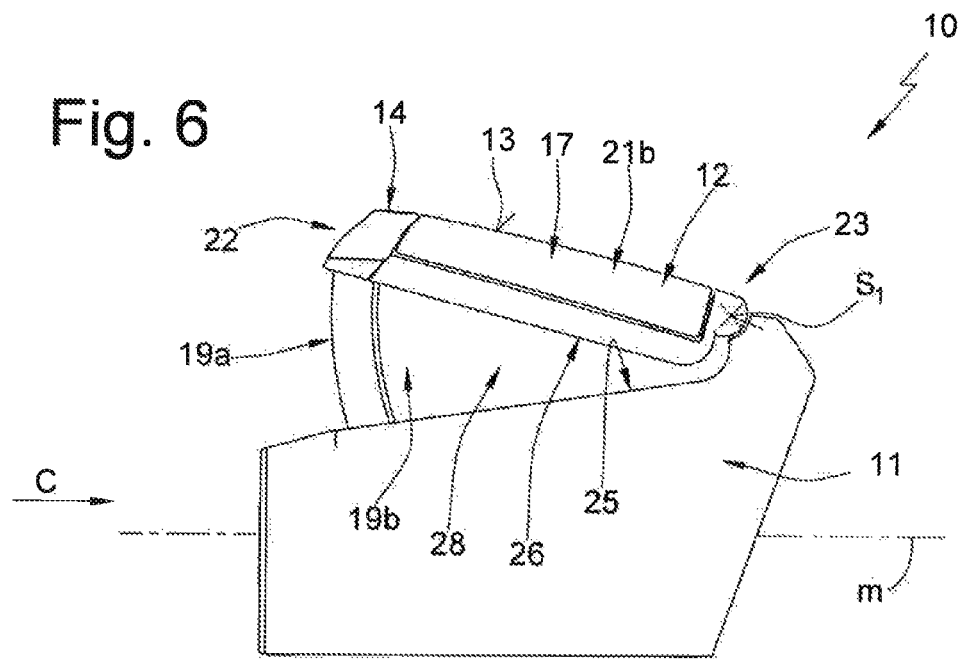
FIG. 6: a side view of the armrest as in FIG. 2.
Figure 7:
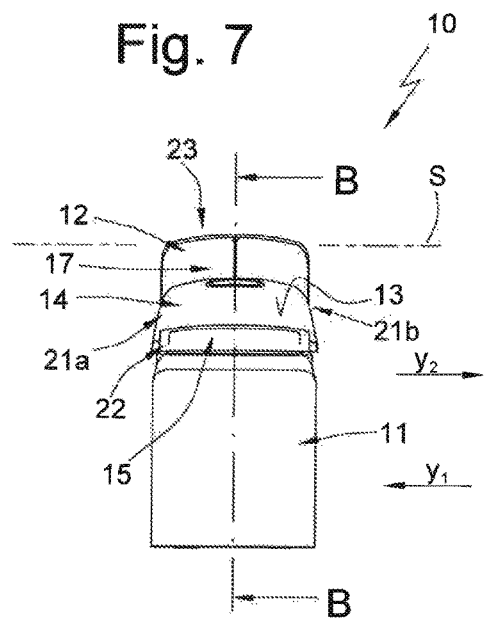
FIG. 7: a view according to arrow A in FIG. 5.

According to FIGS. 5 and 6, in the lower end position of the arm support 12 a lower face 26 of the arm support 12 lies in contact with an upper support face 25 of the base 11. As can be seen in FIGS. 2, 4, 6 and 10, in the upper end position as well as in intermediate positions between the lower end position and the upper end position the upper support face 25 is at a spacing from the lower face 26. An intermediate space between the support face 26 and the face 25 is covered by housing walls 19a, 19b and 19c.

Figure 8:
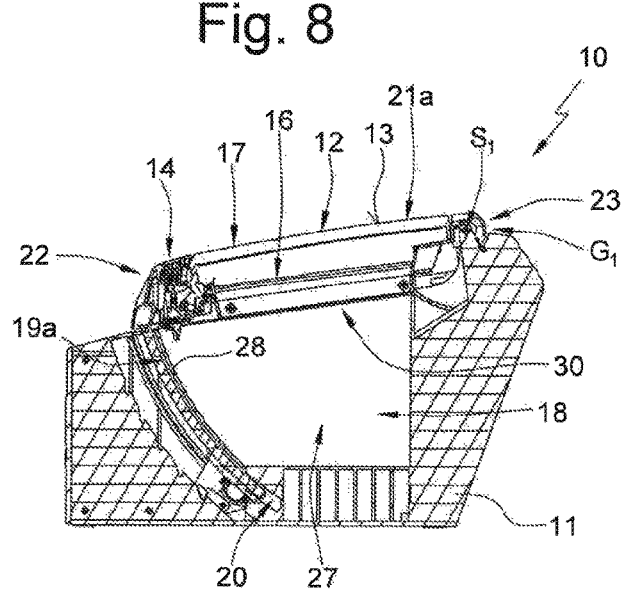
FIG. 8: a sectional view according to section line B-B in FIG. 7.
Figure 9:
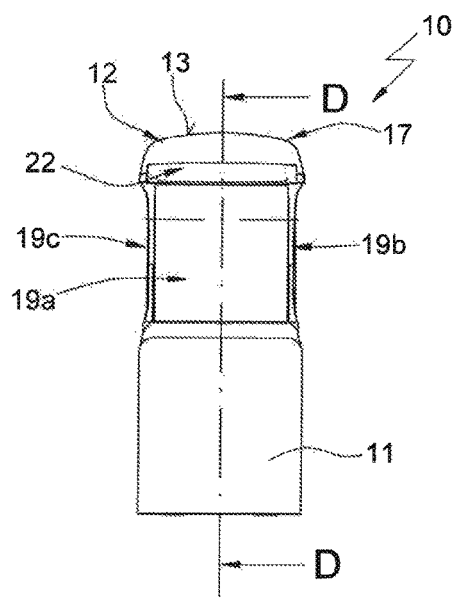
FIG. 9: a view according to arrow C in FIG. 6.

According to FIG. 8, the base 11 comprises a container 18 forming a cavity 27 and an opening 30 facing the lid 17. The cavity 27 is accessible via the opening 16 of the lid and the opening 30 of the container 18 when the lid 17 is in its open position. In the closed position of the lid 17, the cavity 27 is completely closed off and inaccessible to a user.

The housing wall 19a forms a partition of the cavity 27 in the direction $x_1$ and the housing walls 19b and 19c form partitions in the directions $y_1$ and $y_2$. In this way, an additional space arises between the housing walls 19a, 19b and 19c, the pivot joint $G_1$ and between the arm support 12 and the container 18, forming a passage 29 to the cavity 27 that is accessible via the opening 16. The housing walls 19b and 19c are formed approximately at right angles to the housing wall 19a.

All the housing walls 19a, 19b and 19c are fastened to the arm support 12 and connected thereto so as to move therewith. The housing wall 19a is fastened to the front end region 22 and the housing walls 19b and 19c are fastened to the side regions 24a and 24b of the arm support 12. According to the embodiment, the housing walls 19a, 19b and 19c are formed by one part. Alternatively, however, they can also be formed separately.

Figure 10:
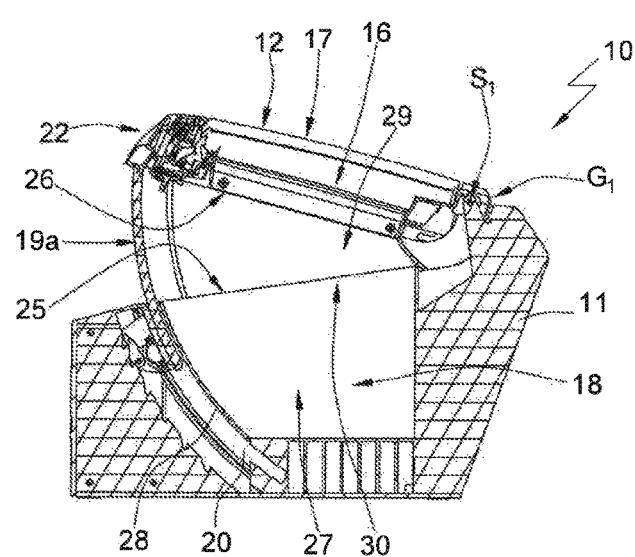
FIG. 10: a sectional view according to section line D-D in FIG. 9.

A slot 20 is allocated to each housing wall 19a, 19b and 19c, of which only one slot 20 is visible in FIGS. 8 and 10 that serves as a stowage space for the housing wall 19a. In all positions of the arm support 12 between the lower end position and the upper end position, at least a region of each housing wall 19a, 19b and 19c is in the respective slot 20. Thus, each housing wall 19a, 19b and 19c closes the cavity 27 of the container 18 and forms the passage 29.

Each slot 20 forms a wall 28 to the cavity 27, so that parts located in the cavity 27 cannot come into contact with the housing walls 19a, 19b and 19c, thereby being damaged or impairing the movability of the arm support 12.

The invention claimed is:

1. An armrest for a vehicle seat, the armrest comprising:
   a base having an upper support face, forming a cavity opening upward at the upper support face, and formed with an upwardly open slot at least partially surrounding the cavity and open at the upper support face;
   an arm support having a lower face and pivotable relative to the base between a lower end position with the lower face resting on the upper support face of the base and an upper end position spaced above the upper support face;
   an upwardly directed arm support face on the arm support; and
   a housing wall carried on and projecting downward from the arm support into the slot around the cavity, the housing wall being connected to the arm support so as to move therewith in such a way that it closes an intermediate space formed between the lower face of the arm support and the upper support face on the base when the arm support pivots up, the arm support being formed with an opening through which access to the cavity is possible, the housing wall being accommodated in the slot in each position between the lower end position and the upper end position of the arm support.

2. The armrest according to claim 1, further comprising:
   a lid engageable over the opening and movable between an open position giving access to the opening and a closed position blocking the opening.

3. The armrest according to claim 2, wherein an outer face of the lid forms at least part of the arm support face.

4. The armrest according to claim 1, wherein the opening is in a region of the arm support face.

5. The armrest according to claim 1, wherein the slot forms a wall of the cavity.

6. The armrest according to claim 1, wherein the housing wall is formed by a plurality of panels formed in one piece or separately.

7. The armrest according to claim 1, wherein the lid comprises two lid parts each pivotable about a pivot axis that extends parallel to a longitudinal axis of the armrest.

8. The armrest according to claim 1, wherein the arm support is movable between the lower position and the upper position through a pivot angle of about 45°.

9. The armrest according to claim 1, further comprising at a front end region of the arm support
   a control panel on which a seat occupant can control operating elements.

10. The armrest according to claim 1, wherein the housing wall forms a passage in such a way that the interior space is accessible only via the opening of the arm support and the passage.

11. The armrest according to claim 1, wherein the arm support and arm support face are pivotal about a horizontal axis at a rear end of the armrest, the housing wall being of U-shape and having a pair of flat side sections flanking the cavity and a front-end section bridging front ends of the side sections.

12. The armrest according to claim 11, wherein the slot is upwardly open and U-shaped complementary to the housing wall.

13. The armrest according to claim 12, wherein the U-shaped slot has an inner wall forming an outer wall of the cavity.

* * * * *